(12) United States Patent
Hagiwara

(10) Patent No.: US 10,695,464 B2
(45) Date of Patent: Jun. 30, 2020

(54) MEDICAL BASE MATERIAL

(71) Applicant: Akeo Hagiwara, Shiga (JP)

(72) Inventor: Akeo Hagiwara, Shiga (JP)

(*) Notice: Subject to any disclaimer, the term of this patent is extended or adjusted under 35 U.S.C. 154(b) by 0 days.

(21) Appl. No.: 15/964,343

(22) Filed: Apr. 27, 2018

(65) Prior Publication Data

US 2018/0289864 A1  Oct. 11, 2018

Related U.S. Application Data

(63) Continuation of application No. PCT/JP2016/081746, filed on Oct. 26, 2016.

(30) Foreign Application Priority Data

Oct. 30, 2015 (JP) .................................. 2015-214595

(51) Int. Cl.
*A61L 27/50* (2006.01)
*A61F 2/06* (2013.01)
(Continued)

(52) U.S. Cl.
CPC .............. *A61L 27/507* (2013.01); *A61F 2/06* (2013.01); *A61F 2/062* (2013.01); *A61L 27/18* (2013.01);
(Continued)

(58) Field of Classification Search
CPC ........ A61L 27/507; A61L 27/00; A61L 27/58; A61L 27/54; A61L 31/10; A61L 2300/604; A61F 2/06; A61F 2/062; A61F 2/91
See application file for complete search history.

(56) References Cited

U.S. PATENT DOCUMENTS

2010/0125330 A1* 5/2010 Belenkaya .............. A61L 27/18
  623/1.46
2013/0085563 A1* 4/2013 Stankus ................ A61L 31/041
  623/1.15

FOREIGN PATENT DOCUMENTS

JP 4-146745 5/1992
JP 5-269196 10/1993
(Continued)

OTHER PUBLICATIONS

International Search Report dated Dec. 20, 2016 in International (PCT) Application No. PCT/JP2016/081746.
(Continued)

*Primary Examiner* — Christopher D. Prone
*Assistant Examiner* — Tiffany P Shipmon
(74) *Attorney, Agent, or Firm* — Wenderoth, Lind & Ponack, L.L.P.

(57) ABSTRACT

Provided is a medical base material that is suitable for regeneration of a cardiovascular system being exposed to high pressure from a lumen, such as an aorta and is absorbed by a living body after transplantation. The medical base material of the present invention has a sheet shape, a tube shape, or a combined shape thereof and is used for regeneration of a cardiovascular system by being transplanted in a body. The medical base material has a multilayer structure at least including an inner layer to be arranged on the intimal side of the cardiovascular system and an outer layer to be arranged on the adventitial side of the cardiovascular system from the inner layer and made from a material at least including a stereo complex polylactic acid. The layer to be arranged on the adventitial side of the cardiovascular system from the inner layer is formed in a porous form such that a nutrient blood vessel reaches the inner layer or enters the vicinity of the inner layer.

12 Claims, 8 Drawing Sheets

(51) Int. Cl.
- *A61L 27/34* (2006.01)
- *A61L 27/56* (2006.01)
- *A61L 27/18* (2006.01)
- *A61L 27/58* (2006.01)
- *A61F 2/91* (2013.01)
- *A61L 27/54* (2006.01)
- *A61L 31/10* (2006.01)

(52) U.S. Cl.
CPC ............... *A61L 27/34* (2013.01); *A61L 27/56* (2013.01); *A61L 27/58* (2013.01); *A61F 2/91* (2013.01); *A61L 27/54* (2013.01); *A61L 31/10* (2013.01); *A61L 2300/604* (2013.01)

(56) References Cited

FOREIGN PATENT DOCUMENTS

| | | |
|---|---|---|
| JP | 2000-17163 | 1/2000 |
| JP | 2005-261867 | 9/2005 |
| JP | 2013-31595 | 2/2013 |
| JP | 2016-158765 | 9/2016 |
| WO | 2007/116646 | 10/2007 |

OTHER PUBLICATIONS

International Preliminary Report on Patentability dated May 1, 2018 in International (PCT) Application No. PCT/JP2016/081746.

* cited by examiner

MEDICAL BASE MATERIAL

TECHNICAL FIELD

The present invention relates to a medical base material, in particular, a medical base material suitable for cardiovascular regeneration.

BACKGROUND ART

In recent years, along with the aging of society and the westernization of food culture, the number of patients with lifestyle diseases is increasing. Arteriosclerosis is also one of lifestyle diseases, and if the symptoms progress, a disease that affects human life, such as an aortic aneurysm, may be developed. If the symptom of the aortic aneurysm progresses, in order to prevent its rupture, the aorta including the lesion site is replaced with an artificial blood vessel by blood vessel prosthesis implantation surgery.

The artificial blood vessel, of course, should not leak plasma as well as blood cells and is also required to have compatibility with human bodies, durability, and safety and must be able to be easily anastomosed with a blood vessel by surgery.

Accordingly, a variety of artificial blood vessels save been developed conventionally. For example, a fabric artificial blood vessel made by knitting or plain weaving a polyester fiber or a polytetrafluoroethylene (PTFE) artificial blood vessel having numerous fissures made by rapidly stretching tubular-shaped PTFE is generally used (see NPL 1).

An artificial blood vessel including an inner layer constituted of a nonwoven fabric layer of an ultrafine fiber having a diameter of 10 μm or less formed by an electrospinning method and a cover material disposed on the outside of the inner layer, wherein the nonwoven fabric layer and the cover material are firmly adhered to each other, has been developed (see PTL 1).

However, these artificial blood vessels are not absorbed by living bodies even after transplantation. Accordingly, if an artificial blood vessel is infected due to, for example, dental treatment, the treatment is very difficult, and surgery for replacement of the artificial blood vessel may be necessary. In addition, since nutrient blood vessels cannot enter the artificial blood vessel, the intimal cells migrating to the lumen of the artificial blood vessel may necrotize.

Accordingly, in recent years, artificial blood vessels made from bioabsorbable fibers that are absorbed in the bodies after transplantation have also been developed. However, existing bioabsorbable artificial blood vessels are constituted of bioabsorbable fibers having rapid biodegradation and absorption rates, such as a copolymer of lactic acid and caprolactone, so as to be decomposed and absorbed promptly after transplantation (see PTL 2).

Accordingly, the strength of the artificial blood vessels is also rapidly decreased, and the artificial blood vessels cannot be used in a cardiovascular system that is always exposed to high pressure from the lumen, such as an artery. Even if such an artificial blood vessel is used in an artery or the like, since the artery or the like is replaced with a diseased tissue, such as a scar tissue, calcification, or an aneurysm, complete regeneration or treatment is not achieved.

CITATION LIST

Patent Literature

PTL 1: Japanese Unexamined Patent Application Publication No. 2013-031595
PTL 2: Japanese Unexamined Patent Application Publication No. 2016-158765

Non Patent Literature

NPL 1: "Artificial blood vessel", Japanese Society for Artificial Organs, [on line], [searched on Oct. 22, 2015], Internet <URL: http://www.jsao.org/public/7.html>

SUMMARY OF INVENTION

Technical Problem

It is an object of the present invention to provide a medical base material that is suitable for regeneration of a cardiovascular system being exposed to high pressure from a lumen, such as an artery, and is absorbed by a living body after transplantation.

Solution to Problem

The present inventor has diligently studied based on the following findings (1) to (4) to solve the problems described above and has arrived at the present invention.

(1) In the treatment of external wound in the plastic surgery field, the dermal part is usually sutured with a bioabsorbable thread that gradually deteriorates the strength over a sufficiently long period of time until decomposition and absorption to be absorbed by a living body. If a bioabsorbable thread that is rapidly absorbed is used, the biological tissue of the wound site is not regenerated or recovered to a skin like the original, but is replaced with a diseased tissue, such as a scar tissue.

(2) In the pediatric cardiac surgery field, for example, in a surgical operation for reconnecting the naturally malformed aorta connected to an abnormal position to a proper position, it is necessary to suture with, for example, a bioabsorbable thread that gradually deteriorates the strength over a sufficiently long period of time until decomposition and absorption to foe absorbed by a living body from the viewpoints of growth and blood pressure after the operation. If a suture thread that is rapidly absorbed is used, the artery is not regenerated or recovered to an artery like the original, but is replaced with a diseased tissue, such as a scar tissue, calcification, or an aneurysm.

(3) In the case of use in, for example, an artery exposed to high pressure from the lumen, even if a conventionally used bioabsorbable suture thread of a polymer, such as polydioxanone, that is considered to have relatively low decomposition and absorption rates is used, the absorption rate is too high.

(4) Stereo complex polylactic acid gradually deteriorates the strength over a sufficiently long period of time, compared to polydioxanone and so on, and is then absorbed.

That is, the medical base material of the present invention has a sheet shape, a tube shape, or a combined shape thereof and is used for regeneration of a cardiovascular system by being transplanted in a body. The medical base material has a multilayer structure at least including an inner layer to be arranged on the intimal side of the cardiovascular system and an outer layer to be arranged on the adventitial side of the cardiovascular system from the inner layer and made from a material at least including a stereo complex polylactic acid. The layer to be arranged on the adventitial side of the cardiovascular system from the inner layer is formed in a porous form such that a nutrient blood vessel reaches the inner layer or enters the vicinity of the inner layer.

The outer layer of the medical base material of the present invention may be constituted of a fabric made from a fiber material containing 50% by weight or more of a stereo complex polylactic acid. The fabric constituting the outer layer is preferably a woven or knitted fabric when the diameter, arrangement, and distribution of pores into which nutrient blood vessels enter are desired to be as uniform as possible.

The inner layer of the medical base material of the present invention may be constituted of at least one material selected from the group consisting of polyglycolic acid, copolymers of lactic acid and caprolactone, L-polylactic acid, D-polylactic acid, copolymers of glycolic acid and lactic acid, gelatin, collagen, and elastin. The inner layer may be constituted of a fabric made from a fiber material. The fabric constituting the inner layer may be a nonwoven, woven, or knitted fabric.

Advantageous Effects of Invention

The medical base material of the present invention is absorbed by a living body after that a nutrient blood vessel enters the medical base material from the adventitial side of a cardiovascular system and intimal cells migrate to the intimal side of the cardiovascular system while the outer layer retains its shape against the pressure of, for example, blood over a long period of time. Accordingly, when the medical base material of the present invention is used in, for example, an artificial blood vessel, for example, an aorta that is always exposed to high pressure from a lumen can be well regenerated and replacement by retransplantation is not needed later.

DESCRIPTION OF EMBODIMENTS

1. Medical base material

The medical base material of the present invention has a sheet shape, a tube shape, or a combined shape thereof and is used for regeneration of a cardiovascular system by being transplanted in a body by treatment such as a surgical operation, as in an artificial blood vessel, an intravascular stent, or an intravascular stent graft.

The medical base material of the present invention can be used for regeneration of a cardiovascular system, for example, blood vessels such as an artery and a vein, heart, and a lymphatic vessel and can stably regenerate an artery that takes a long time to be regenerated and receives blood pressure and also can stably regenerate an aorta that receives high artery blood pressure.

Accordingly, cases of using the medical base material of the present invention as an artificial blood vessel will now be described based on drawings. The use of the medical base material of the present invention is not limited to artificial blood vessels.

Figure 1A:
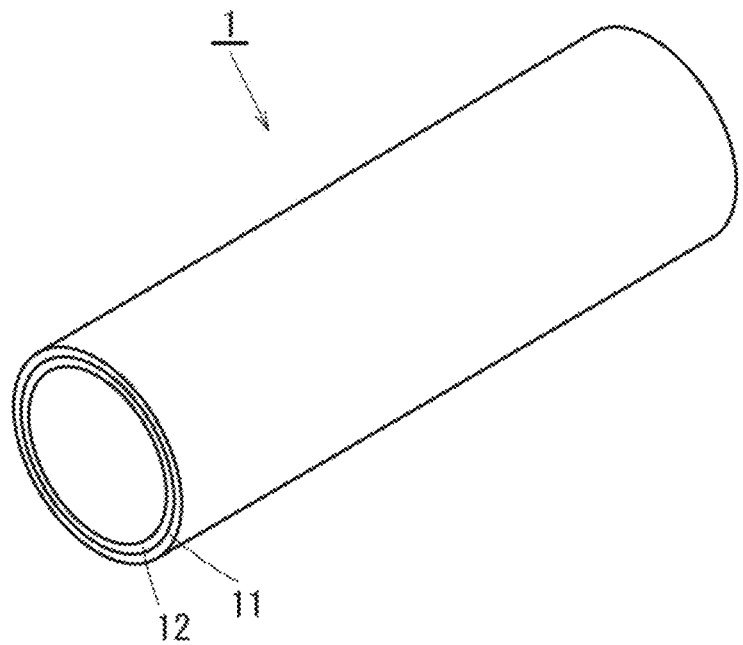
FIG. 1A is an external perspective view of a medical base material according to the present invention.
Figure 1B:
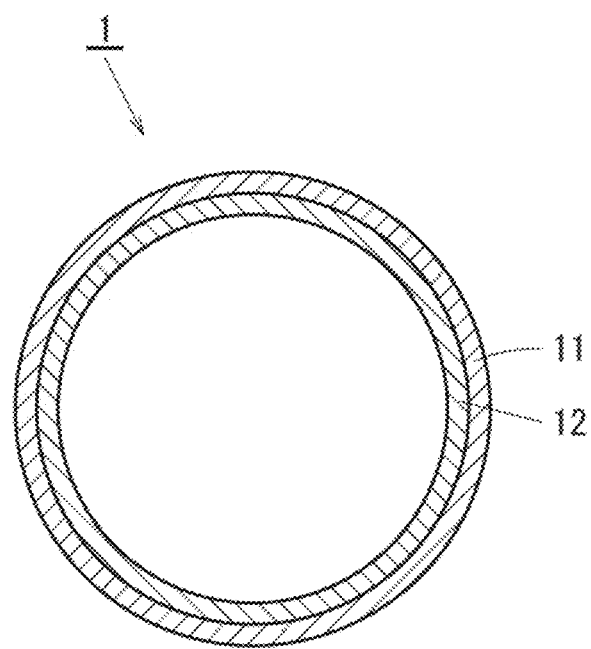
FIG. 1B is a cross-sectional view of the medical base material according to the present invention.

FIG. 1A is an external perspective view of a medical base material 1 according to the present invention. FIG. 1B is a cross-sectional view of the medical base material 1 according to the present invention. As shown in FIGS. 1A and 1B, the medical base material 1 includes an outer layer 11 and an inner layer 12 disposed on the inner side from the outer layer 11. Herein, the inner layer 12 may be unified with the outer layer 11 or may be layered in multiple layers. Such a medical base material 1 can be produced by, for example, separately producing each layer and then fitting them manually or with a known device.

2. Outer layer

The outer layer 11 constituting the medical base material 1 of the present invention is a hollow cylindrical fabric made from a fiber containing a stereo complex polylactic acid. The outer layer 11 should have a strength that can stand up to the pressure from a blood vessel lumen and maintain the function of a blood vessel (hereinafter, abbreviated as strength conditions) for a certain period until the inner layer 12 is absorbed by the living body. For example, it is preferred that the outer layer 11 can maintain the strength for at least 3 months, which varies depending on the individual differences of the transplantation recipients, after the transplantation. The outer layer 11 then gradually deteriorates the strength over a sufficiently long period of time along with the progress of the tissue regeneration process and is absorbed by the living body without delay after the completion of the regeneration.

(1) Stereo complex polylactic acid

In the present specification, the term "stereo complex polylactic acid" includes those produced by mixing L-polylactic acid (PLLA) consisting only of L-lactic acid and D-polylactic acid (PBLA) consisting only of D-lactic acid and intertwining the respective helical structures thereof and those produced by mixing block copolymers of L-lactic acid and D-lactic acid respectively connected in block forms and partially intertwining the helical structures of the L-lactic acid chain portion and the D-lactic acid chain portion of the copolymers. The ratio between L-lactic acid and D-lactic acid is not limited to 1:1 and may be a biased ratio, such as 70:30.

The time of starting obvious deterioration in the physical strength of such a stereo complex polylactic acid in a living body (that is, the degree of influence on the structure of the living body that is being regenerated) is later than that of the inner layer 12.

The stereo complex polylactic acid can be produced by, for example, a method described in Japanese Patent No. 5957885, 5821021, 5731207, 5723851, or 5679411. The stereo complex polylactic acid may have any molecular weight that allows the outer layer 11 to maintain the strength conditions.

(2) Fabric

The term "fabric" in the present specification refers to a product prepared by processing a large number of fibers into a thin and wide plate shape and can be classified into a woven, knitted, or nonwoven fabric. As the fiber constituting the outer layer 11, the stereo complex polylactic acid may be used alone or may be used in a mixture with another material that can be decomposed and absorbed by a living body. However, the content of the stereo complex polylactic acid in the fabric is preferably 50% by weight or more for reliably fulfill the strength conditions.

The fiber constituting the fabric may be a monofilament, a twisted yarn, or a roving thread and is preferably a twisted yarn. Examples of the fiber include a fiber made from a stereo complex polylactic acid, a fiber composed of a stereo complex polylactic acid and another material, and a fiber mixture of a fiber made from a stereo complex polylactic acid and a fiber made from another material.

Examples of the material other than a stereo complex polylactic acid include known bioabsorbable polymers, such as polyglycolic acid (hereinafter, abbreviated to PGA in some cases), copolymers of lactic acid and caprolactone (hereinafter, abbreviated to CL in some cases), L-polylactic acid, D-polylactic acid, copolymers of glycolic acid and lactic acid, gelatin, collagen, and elastin.

The weight ratio of the monomers constituting the bioabsorbable polymer is not particularly limited within a range fulfilling the strength conditions. In addition, a single bioabsorbable polymer may be used or a mixture of two or more bioabsorbable polymers may be used as long as the strength conditions are fulfilled.

The fabric constituting the outer layer 11 is not particularly limited and can be produced by a known method from, for example, a stereo complex polylactic acid. Specifically, the fabric may be produced as a woven fabric or a knitted fabric (including a net-like fabric, the same shall apply hereinafter unless otherwise specified) with a known weaving machine or knitting machine or may be produced as a nonwoven fabric by a known method such as an electrospinning method or a melt-blow method.

When the fabric constituting the outer layer 11 is made from a fiber material as in a woven, knitted, or nonwoven fabric, the fiber constituting the fabric may have any fiber length, fiber diameter, and ratio of the diameter to the length within ranges fulfilling the strength conditions. However, considering the strength conditions, the fiber diameter is preferably 0.1 to 40 μm and more preferably 0.5 to 20 μm as the median.

In a cross-section of a fabric, the distance from the stump of an arbitrary fiber to the stump of an adjacent fiber (hereinafter, abbreviated as fiber interval) varies depending on the structure of the fabric. Specifically, in a nonwoven fabric, the fiber interval is preferably 5 to 1000 μm and more preferably 15 to 500 μm as the median. If the distance is smaller than 5 μm, the infiltration and fixation of cells and, particularly, a nutrient blood vessel are difficult, and the self-organization of the fabric including a blood vessel for regenerating an aorta is difficult. A distance of larger than 1000 μm has a risk of leakage of blood or the like from the medical base material 1 due to internal pressure such as blood pressure. In a woven or knitted fabric, the fiber interval is preferably 15 to 2000 μm and more preferably 30 to 1500 μm from the same reasons.

When multiple outer layers are disposed around the inner layer or when the medical base material includes an intermediate layer described below, the fiber constituting the outer layer may have a fiber interval of 1 to 4 mm.

The fiber length, the fiber diameter, the ratio of the diameter to the length, and the fiber interval of the fibers constituting the fabric may be each a single value, but preferably vary. Because (a) such variations are advantageous for cell proliferation and tissue regeneration in imitation of the fibers constituting the extracellular structure in a living body and (b) different deterioration rates according to the variations cause a gradual change in the strength of the regeneration tissue to reduce the risk of shape abnormalities (abnormal enlargement, rupture, stenosis, and occlusion) and constitution abnormalities (e.g., scarring and calcification) of the regeneration tissue.

(4) Method of measurement

The fiber diameter and the fiber interval of the fibers constituting the fabric, shown in the paragraph (3) are medians of the values measured as follows. The median is one of representative values and is a value located in the center when a finite size of the data is arranged in order of magnitude. When the size of the data is an even number, the median is the arithmetic average of two values close to the center.

1) Knitted fabric or woven fabric case (a) Fiber diameter

The fiber diameter of a knitted fabric or a woven fabric is determined as follows. A fabric is cut, and the cut section is photographed with an optical microscope (20× to 100× magnification). Subsequently, the photographed image is taken into a computer image system, and the fiber diameter is measured using distance measurement software (theoretically measurable down to 0.01 μm).

In a woven fabric and a knitted fabric, a plurality of monofilament fibers is bundled into one weaving yarn or knitting yarn. Accordingly, the fiber diameters of 50 randomly selected monofilaments each having a true circular cross-section are measured, and the median thereof is defined as the fiber diameter of the fabric.

(b) Fiber interval

The fiber interval of a knitted fabric or a woven, fabric, is determined as follows. The surface of a fabric is photographed with a stereomicroscope (a magnification of 10× or less, light source irradiation from both the front and back sides). The photographed image is taken into a computer image system, and the fiber interval is measured from the taken image using distance measurement software (theoretically measurable down to 0.01 μm).

In a woven fabric and a knitted fabric, a plurality of monofilament fibers is bundled into one weaving yarn or knitting yarn. Accordingly, the fiber interval is determined based OR the size of a weave (stitch) formed between the edges of adjacent weaving yarns (or knitting yarns). Since the weave (or stitch) has a substantially triangular, quadrangular, or pseudo circular shape, the method for determining the fiber interval in each case is described below. A complicated case where weaves (or stitches) have various shapes and sizes is described in each description.

In a weave (or stitch) having a substantially triangular shape, the shape is regarded as a triangle, and the average of the three heights of the triangle is defined as the fiber interval of the triangle. The median of the fiber intervals of 30 randomly selected triangles is defined as the fiber interval of the fabric.

In a weave (or stitch) having a substantially quadrangular shape, the average of the maximum value and the minimum value of the distance between a pair of opposing sides and the average of the maximum value and the minimum value of the distance between another pair of opposing sides are determined. The weighted average of these four values is defined as the fiber interval of the quadrangle. The median of the fiber intervals of 30 randomly selected quadrangles is defined as the fiber interval of the fabric.

In a weave (or stitch) having a pseudo circular shape, the shape is regarded as a circle, and the diameter of the circle is defined as the fiber interval of the circle. The median of the fiber intervals of 30 randomly selected pseucio circles is defined as the fiber interval of the fabric.

2) Nonwoven fabric case (a) Fiber diameter

The fiber diameter of a nonwoven fabric is determined as follows. A nonwoven fabric to be measured is frozen and hardened in liquid nitrogen and is then cut. Subsequently, the cut section of the nonwoven fabric is photographed with a scanning electron microscope. The diameters of the stumps of 50 fibers randomly selected from many fiber cross-sections exposing to the cut section of the nonwoven fabric are measured. The median of the measured fiber diameters is defined as the fiber diameter of the nonwoven fabric.

(b) Fiber interval

The fiber interval of a nonwoven fabric is determined as follows. A nonwoven fabric to be measured is frozen and hardened in liquid nitrogen and is then cut. Subsequently, the cut section of the nonwoven fabric is photographed with a scanning electron microscope. One fiber is randomly selected from many fiber cross-sections exposing to the cut section of the nonwoven fabric, and 30 other fibers are selected in order of distance from the fiber selected above. The fiber distances from the fiber selected above are measured, and the median of the measured fiber distances is calculated. Similarly, three medians are determined for one nonwoven fabric, and the median of the determined three medians is defined as the fiber interval of the nonwoven fabric.

3. Inner layer

The inner layer 12 constituting the medical base material 1 of the present invention is constituted of a highly biocompatible fabric and enhances the migration of cells such as endothelial cells, without maintaining the external shape of the medical base material 1, and enhances the self-regeneration of a cardiovascular system, such as an aorta, and is finally replaced with, for example, vascular endothelial cells. The term "highly biocompatible" means that, the compatibility is high compare to the material of the outer layer 11. Accordingly, the inner layer 12 has higher bioabsorbability than the outer layer 11 and is preferably absorbed by a living body within, for example, about one to twelve months.

(1) Highly biocompatible fabric

The material of the highly biocompatible fabric constituting the inner layer 12 may be any material having high biocompatibility compared to the material of the outer layer 11, and examples thereof include known bioabsorbable polymers, such as polyglycolic acid, copolymers of lactic acid and caprolactone, L-polylactic acid, D-polylactic acid, copolymers of glycolic acid and lactic acid, gelatin, collagen, and elastin.

The weight ratio of the monomers constituting the bioabsorbable polymer is not particularly limited within a range fulfilling the high biocompatibility. In addition, a single bioabsorbable polymer may be used or a mixture of two or more bioabsorbable polymers may be used as long as the high biocompatibility is fulfilled.

The highly biocompatible fabric constituting the inner layer 12 may be any fabric fulfilling the high biocompatibility and can be produced by a known method. Specifically, the highly biocompatible fabric may be produced as a woven fabric or a knitted fabric with a known weaving machine or knitting machine or may be produced as a nonwoven fabric by a known method, such as an electrospinning method or a melt-blow method.

When the fabric constituting the inner layer 12 is made from a fiber material as in a woven, knitted, or nonwoven fabric, the fiber constituting the fabric may have any fiber length, fiber diameter, and ratio of the diameter to the length within ranges fulfilling the high compatibility. However, the fiber diameter is preferably 20 µm or less and more preferably 10 µm or less as the median, because a too large fiber diameter is apt to cause, for example, turbulence of blood and increases the risk of occlusion of the vascular lumen due to thrombogenesis.

The highly biocompatible fabric constituting the inner layer 22 preferably has a fiber interval of 100 µm or less and more preferably 60 µm or less as the median. When the inner layer 22 is of a porous material, the fiber interval (pore diameter) is preferably 200 µm or less and more preferably 100 µm or less as the median. If a highly biocompatible fabric having a large fiber interval (pore diameter) is used in blood vessel regeneration, the risk of occlusion of the blood vessel by thrombogenesis is increased, and leakage of a liquid, such as blood, from the blood vessel wall cannot be prevented.

The fiber length, the fiber diameter, the ratio of the diameter to the length, and the fiber interval of the fiber constituting the highly biocompatible fabric may be each a single value, but preferably vary. The reasons thereof are the same as those in the outer layer 11. The methods of measuring the fiber diameter and the fiber interval of the fiber constituting the highly biocompatible fabric are the same as those in the outer layer 11.

4. Intermediate layer

Figure 2A:
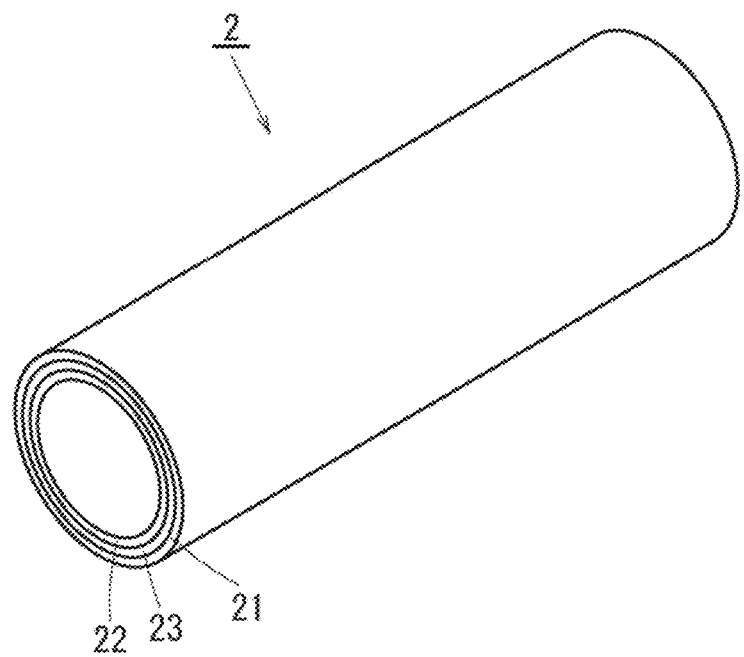
FIG. 2A is an external perspective view of another medical base material according to the present invention.
Figure 2B:
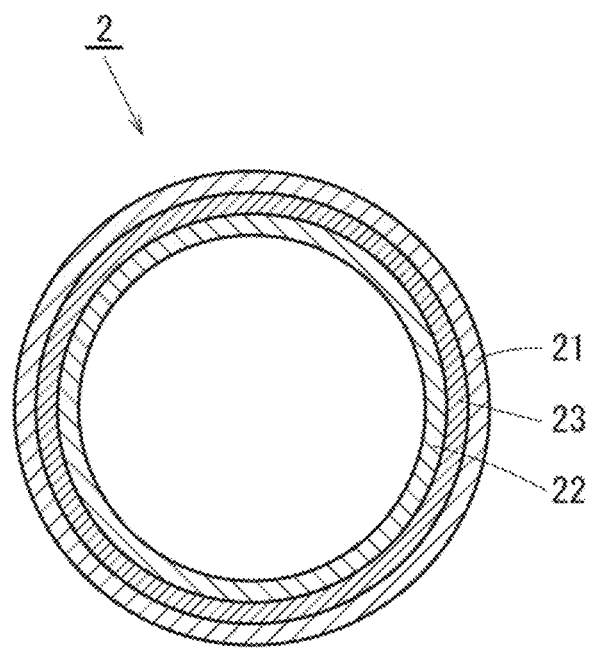
FIG. 2B is a cross-sectional view of another medical base material according to the present invention.

The medical base material of the present invention may include an intermediate layer between the inner layer and the outer layer. FIG. 2A is an external perspective view of another medical base material 2 according to the present indention. FIG. 20 is a cross-sectional view of the medical base material 2 according to the present invention. As shown in FIGS. 2A and 2B, the medical base material 2 includes an outer layer 21, an inner layer 22, and an intermediate layer 23 disposed between the outer layer and the inner layer.

Such a medical base material 2 can be produced by, for example, separately producing each layer and then fitting them manually or with a known device. The outer layer 21 and the inner layer 22 have the same compositions as the outer layer 11 and the inner layer 12 of the medical base material 1, respectively, and the description thereof is therefore omitted.

The intermediate layer 23 is constituted of a biodegradable fabric and assists regeneration of a nutrient blood vessel and a media while maintaining the external shape of the medical base material 2 together with the outer layer 21 and is finally absorbed by a living body (hereinafter, abbreviated as absorption conditions).

The material of the fabric constituting the intermediate layer 23 may be any material fulfilling the absorption conditions and may be a known material. Examples of the material include known bioabsorbable polymers, such as polyglycolic acid, copolymers of lactic acid and caprolactone, L-polylactic acid, D-polylactic acid, copolymers of glycolic acid and lactic acid, gelatin, collagen, and elastin.

The weight ratio of the monomers constituting the bioabsorbable polymer is not particularly limited within a range fulfilling the absorption conditions. In addition, a single bioabsorbable polymer may be used or a mixture of two or more bioabsorbable polymers may be used as long as the absorption conditions are fulfilled.

The fabric constituting the intermediate layer 23 may be any fabric fulfilling the absorption conditions and can be produced by a known method. Specifically, the fabric may be produced as a woven fabric or a knitted fabric with a known weaving machine or knitting machine or may be produced as a nonwoven fabric by a known method, such as an electrospinning method or a melt-blow method.

When the fabric constituting the intermediate layer 23 is made from a fiber material as a woven, knitted, or nonwoven fabric, the fiber constituting the fabric may have any fiber length, fiber diameter, and ratio of the diameter to the length within ranges fulfilling the absorption conditions. However, the fiber of the fabric constituting the intermediate layer 23 preferably has a fiber diameter of 50 μm or less and more preferably 20 μm or less as the median.

The fiber interval of a nonwoven fabric constituting the intermediate layer 23 is preferably 3 to 300 μm and more preferably 5 to 100 μm as the median, and the fiber interval of a woven or knitted fabric constituting the intermediate layer 23 is preferably 15 to 1000 μm and more preferably 30 to 300 μm as the median.

The fiber length, the fiber diameter, the ratio of the diameter to the length, and the fiber interval of the fiber of the fabric constituting the intermediate layer 23 may be each a single value, but preferably vary. The reasons thereof are the same as those in the outer layer 11. The methods of measuring the fiber diameter and the fiber interval of the fiber constituting the fabric are the same as those in the outer layer 11.

The present invention will now be described in more detail based on examples and so on. The present invention is not limited to the following examples and so on in any meaning.

EXPERIMENTAL EXAMPLES

<Experiment 1> Production of fabric

The following four fabrics (1) to (4) were produced: using different raw materials by different producing methods. Specifically, the fabrics were produced as follows. The produced fabrics were sterilized with ethylene oxide gas before use.

(1) ESD (LA/CL) fabric: A nonwoven fabric produced from a copolymer of lactic acid and caprolactone (lactic acid: 50% by weight, caprolactone: 50% by weight) by an electrospinning method and having a relatively small average fiber interval of 6 μm;

(2) ESD-B (LA/CL) fabric: A nonwoven fabric produced from a copolymer of lactic acid and caprolactone (lactic acid: 75% by weight, caprolactone: 25% by weight) by an electrospinning method and having a relatively large fiber interval of 40 μm or more as the median;

(3) ESD (PGA) fabric: A nonwoven fabric produced from polyglycolic acid by an electrospinning method and having a relatively large fiber interval of 40 μm or more as the median; and (4) K (PLA) fabric: Knitted fabrics produced from a fiber of a stereo complex polylactic acid (L-polylactic acid: 50% by weight, D-polylactic acid: 50% by weight, molecular weight: about 90000) and each having a stitch size of 30 to 1500 μm or having a plurality of stitch sizes in a single fabric.

<Experiment 2> Verification of cellular infiltration

The fabrics produced in Experiment 1 were implanted in the skin of rats, and the situations of cell infiltration into the fabrics were investigated. Specifically, the experiment was carried out as follows.

(1) Experimental animal and its acclimation

Female Wister rats each having a weight of 150 g purchased from Shimizu Experimental Animal Co., were used as the experimental animal. All rats were raised under standard conditions (a day/night cycle of 12 hours of light and 12 hours of dark, average temperature: 23° C., average humidity: 50%) and were freely fed with standard feed and water. The rats were raised under this condition for one week before the experiment.

(2) Experimental method

All the following surgical treatments were conducted by a single surgeon under sterile conditions. The rats were each fixed in a prone position under general anesthesia by inhalation of isoflurane and intraperitoneal injection of 30 mg/kg of pentobarbital (Somnopentyl (registered trademark), Kyoritsu Seiyaku Corporation). The back was shaved. The skin was cleaned with an 80% ethanol solution containing 5% chlorhexidine and disinfected with a 10% povidone-iodine solution.

A skin incision of 10 mm was made in the back of each rat, and the subcutaneous tissue was bluntly peeled to create a skin pocket. A fabric was put in the skin pocket at "one fabric for one skin pocket", and the skin pocket was sutured and closed by a single interrupted suture with a 5-0 nylon monofilament suture.

The rats were euthanized by intraperitoneal injection of 100 mg/kg of pentobarbital on the 14th or 21st day after the operation. A U-shaped incision was made in the circumference of the skin pocket, and the fabric including of the regeneration scaffold fabric was surgically resected as a single block to provide a resected specimen. The resected specimen was fixed in a 10% neutral formalin solution and stained with hematoxylin-eosin (hereinafter, abbreviated to HE) by a standard approach to prepare a microscopic thin slice specimen (4 μm). The thin slice specimen was observed under an optical microscope.

(3) Experimental results

Figure 3A:
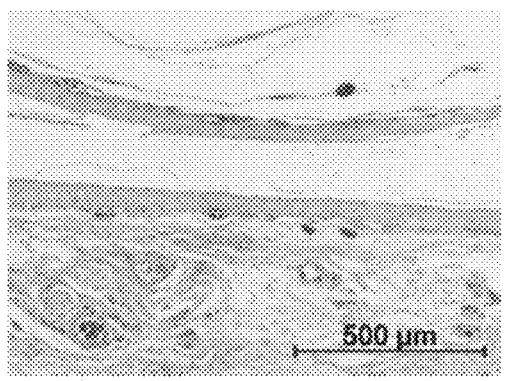
FIGS. 3A to 3D are photographs for drawings showing the results of investigation on the situation of cell infiltration into a fabric constituting a medical base material according to the present invention implanted in the back of rats.
Figure 3C:
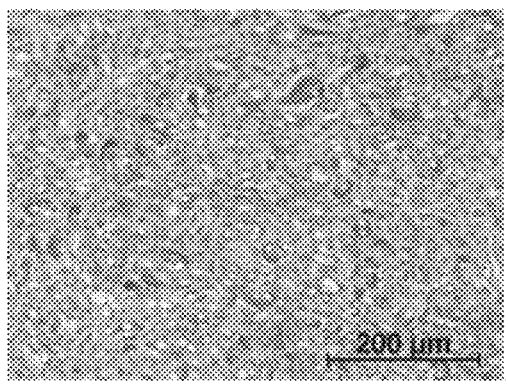
Figure 3B:
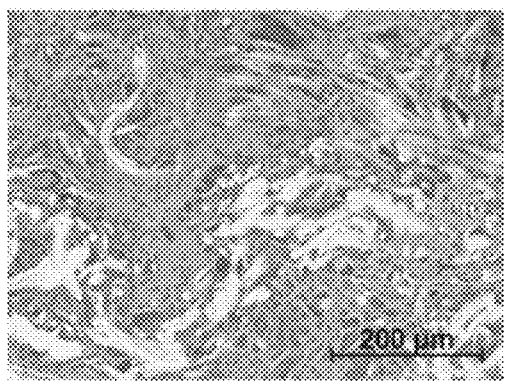
Figure 3D:
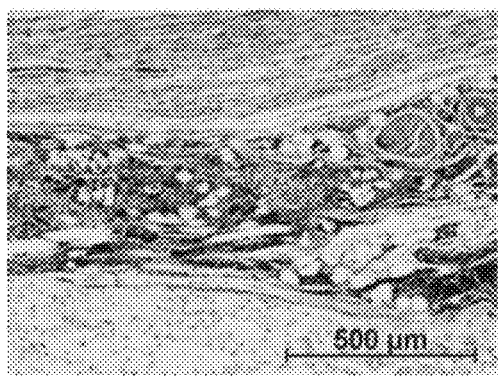

FIGS. 3A to 3D show the results. FIG. 3A shows a microscopic photograph of the resected specimen resected on the 21st day after the implantation of the ESD (LA/CL) fabric; FIG. 3B shows a microscopic photograph of the resected specimen resected on the 14th day after the implantation of the ESD-B (LA/CL) fabric; FIG. 3C shows a microscopic photograph of the resected specimen resected on the 14th day after the implantation of the ESD (PGA) fabric; and FIG. 3D shows a microscopic photograph of the resected specimen resected on the 14th day after the implantation of the K (PLA) fabric.

As shown in FIG. 3A, the cells did not infiltrate into the inside of the ESD (LA/CL) fabric even on the 21st day from the implantation. In contrast to this, as shown in FIG. 3B, FIG. 3C, and FIG. 3D, it was demonstrated that numerous cells infiltrated throughout all layers of the ESD-B (LA/CL) fabric, the ESD (PGA) fabric, and the K (PLA) fabric even on the 14th day after the implantation.

<Experiment 3> Verification of reinforcement layer formation

Whether stromal cells infiltrate into the inside of each fabric produced in Experiment 1 and form a reinforcement layer (self-assembled reinforcement layer) was investigated by investigating the situations of cell infiltration into the fabric tightly wrapped around the iliac artery of each dog. Specifically, the experiment was carried out as follows.

(1) Experimental animal and its acclimation

One-year old female beagle dogs each not being pregnant and having a weight of 10 kg purchased from Shimizu Experimental Animal Co., were used as the experimental animal. During the experimental period, the dogs were raised individually under standard conditions for at least one week before the experiment and were freely fed with standard dog feed and water.

(2) Experimental method

All of the following surgical treatments were conducted by a single surgeon team under sterile conditions. The dogs were basically anesthetized by intravenous anesthesia with 34 mg/kg of pentobarbital. The dogs were subjected to endotracheal intubation with an S-shaped tube and were generally anesthetized by inhalation of 40% oxygen and sevoflurane or isoflurane. Under this general anesthesia, the dogs were fixed in a supine position, and the abdominal hair was shaved. The skin, was cleaned with an 80% ethanol solution containing 5% chlorhexidine and disinfected with a 10% povidone iodine solution.

An abdominal incision wound of 15 cm was made in the middle of the abdomen. The peritoneum on the common iliac artery was incised to expose the iliac artery. The connective tissue surrounding the artery was removed, and the ESD-B (LA/CL) fabric, the ESD (PGA) fabric, or the K (PLA) fabric was tightly wrapped around the artery. The peritoneal incision edges were sutured, then the abdominal incision wound was closed by two-layer suture. For 3 to 7 days after the operation, two types of antibiotics were administered depending on the state of the surgical wound.

Four weeks after the operation, the dogs were euthanized by intravenous injection of 100 mg/kg of pentobarbital. The abdomen was incised again, and the transplanted regeneration scaffold was surgically resected as a single block with the surrounding tissue of the iliac artery to provide a resected specimen. This resected specimen was fixed in a 10% neutral formalin solution and was HE-stained by a standard approach to provide a thin slice specimen (4 µm). The thin slice specimen was observed under an optical microscope.

(3) Experimental results

Figure 4A:
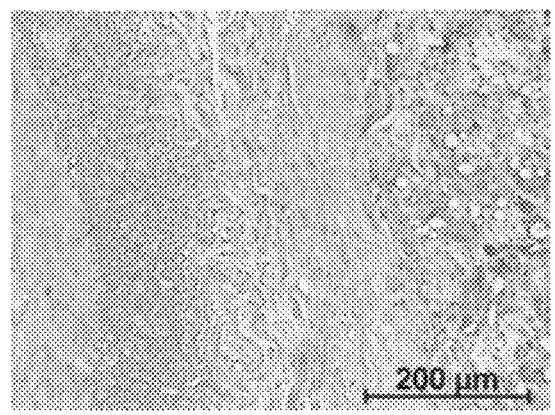
FIGS. 4A to 4C are photographs for drawings showing the results of investigation on whether a fabric constituting the medical base material according to the present invention can form a reinforcement layer when the fabric is tightly wrapped around the iliac artery in dogs.
Figure 4B:
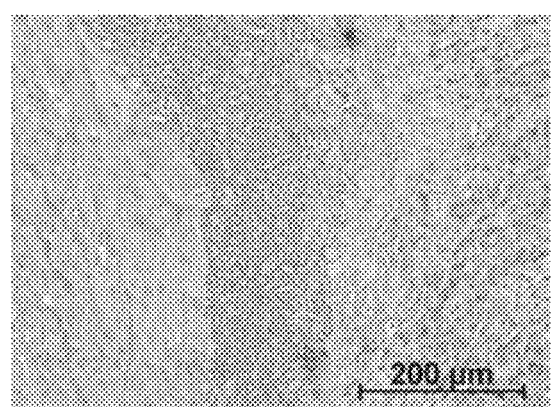
Figure 4C:
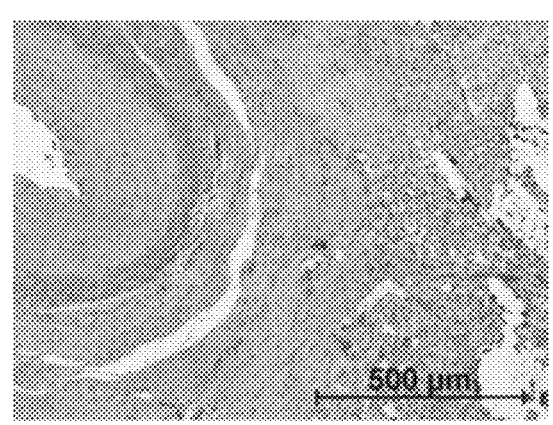

FIGS. 4A to 4C show the results. FIG. 4A shows a microscopic photograph of the resected specimen resected four weeks after wrapping of the ESD-B (LA/CL) fabric; FIG. 4B shows a microscopic photograph of the resected specimen resected four weeks after the wrapping of the ESD (PGA) fabric; and FIG. 4C shows a microscopic photograph of the resected specimen resected four weeks after the wrapping of the K (PLA) fabric.

As shown in FIG. 4A, numerous stromal cells infiltrated throughout all layers of the ESD-B (LA/CL) fabric. As shown in FIG. 4B, numerous stromal cells infiltrated throughout all layers of the ESD (PGA) fabric. In addition, as shown in FIG. 4C, numerous stromal cells infiltrated throughout all layers of the K (PLA) fabric.

The results of this experiment demonstrated that each of the fabrics produced in Experiment 1 is useful for reinforcement of the aortic wall by wrapping it around an aorta.

<Experiment 4> Verification of effect of reinforcing blood vessel of arterial wall incision site Whether the reinforcement layer formed from each of the fabrics produced in Experiment 1 has an effect of reinforcing, the artery wall incision site against the artery blood pressure was investigated by investigating the situations of cell infiltration into the fabric wrapped around the aorta incised a half circumference thereof of the dog. Specifically, the experiment was carried out as follows.

(1) Experimental animal and its acclimation

Dogs were acclimated as in Experiment 3 and were then used.

(2) Experimental method

An abdominal incision was made in each of the dogs as in Experiment 3, and the peritoneum on the aorta was incised. The aorta from the renal arterial branch to the common iliac artery branch was exposed and was peeled from the surrounding tissue. During the peeling, the lumbar artery was being ligated and dissected.

After intravenous injection of 2000 Units of low molecular heparin, the aorta was closed with two forceps, and a half circumference of the aortic wall was incised between the forceps. The aortic lumen was washed with heparin-physiological saline, and the aortic wall incision edges were sutured by three single interrupted sutures with 6-0 polypropylene.

In order to reinforce the sutured wall, the K (PLA) fabric was tightly wrapped three times around the aortic wall along this suture line and was pressed with fingers for 5 minutes to stop bleeding. The peritoneal incision edges were sutured, then the abdominal incision wound was closed by two-layer suture. After the operation, anticoagulation was performed with 2000 Units of low molecular heparin and 100 mg of aspirin or 1 mg of warfarin per day.

Four weeks after the operation, the dogs were euthanized by intravenous injection of 100 mg/kg of pentobarbital. The abdomen was incised again, and the transplanted regeneration scaffold (the fabric) was surgically resected as a single block with the surrounding tissue of the aorta to provide a resected specimen. This resected specimen was evaluated with naked eyes and was then fixed in a 10% neutral formalin solution and was HE-stained by a standard approach to provide a thin slice specimen (4 µm). This thin slice specimen was observed under an optical microscope.

(3) Experimental results

As the results of naked-eye observation, no bleeding was observed in the circumference of the incision wound of the aorta. That is, when a half circumference of an aortic wall was incised and sutured by three interrupted sutures and the K (PLA) fabric was then wrapped around the incision wound, it was revealed that the K (PLA) fabric reinforced the incision wound site within four weeks, well repaired the incision edge, and prevented bleeding from the aorta against the blood pressure. It has long been known that mere suturing by three interrupted sutures cannot prevent massive bleeding from the incision wound site against blood pressure.

Figure 5A:
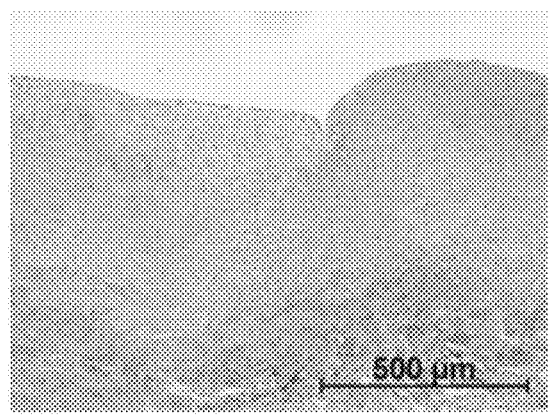
FIGS. 5A and 5B are photographs for drawings showing the results of investigation on whether a reinforcement layer formed by a fabric constituting the medical base material according to the present invention can reinforce the arterial wall stump suture site when the fabric is wrapped around the aorta incised a half circumference thereof in dogs.
Figure 5B:
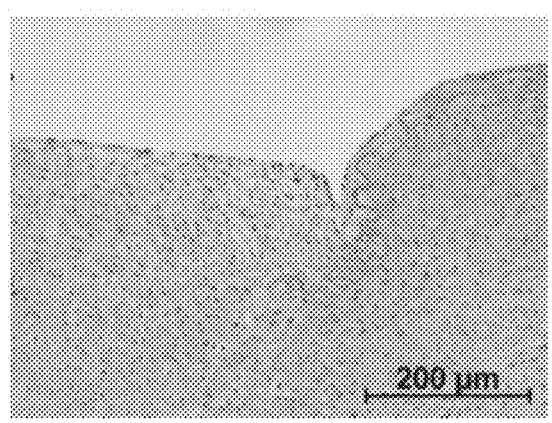

FIGS. 5A and 5B show the results of microscopic observation. FIG. 5A shows a microscopic photograph of the incision wound edge portion of a resected specimen resected four weeks after the wrapping with the K (PLA) fabric; and FIG. 5B shows a partially enlarged view thereof.

As shown in FIGS. 5A and 5B, the intima and the media were regenerated, and since the incision wound edge was flat, and did not have an aneurysm, the aortic wall incision wound edge was well repaired.

These results demonstrated that when the K (PLA) fabric produced in Experiment 1 was wrapped around the aortic wall incision wound edge, the aorta incision wound edge was reinforced within four weeks against the blood pressure of the aorta and was well repaired.

<Experiment 5> Verification of usability in regeneration scaffold

Whether each of the fabrics produced in Experiment 1 can be used as a regeneration scaffold of the aorta of dogs was investigated by investigating the situation of cell infiltration into the fabric wrapped around the completely dissected portion along the whole circumference of the aorta peripheral wall of the dog. Specifically, the experiment was carried out as follows.

(1) Experimental animal and its acclimation

Dogs were acclimated as in Experiment 3 and were then used.

(2) Experimental method

The aorta was peeled from the surrounding tissue as in Experiment 4, and the aorta was held with two forceps. The aorta was completed dissected between the forceps along the whole circumference of the aortic wall. The two stumps of the aorta were washed with heparin-physiological saline. An ESD (LA/CL) fabric tube (inner layer) having a length of 4 cm and a diameter of 8 mm was placed between the two stumps of the aorta, and the edges of the aorta and the tube were anastomosed. That is, the tube stump and the aortic wall stump were sutured with 12 of a 6-0 polypropylene monofilament sutures.

The K (PLA) fabric in a cylindrical shape (outer layer) having a length of 5 to 15 cm was wrapped on the tube and the anastomosed site with a width of 6 cm for reinforcement. Furthermore, the ESD (PGA) fabric having a width of 3 cm was wrapped around the anastomosed site twice for protection (protective layer). Finally, the peritoneal incision edges were sutured, and then the abdominal incision wound was closed by two-layer suture. After the operation, anticoagulation was performed with 2000 Units of low molecular heparin and 100 mg of aspirin or 1 mg of warfarin per day.

Ten months after the operation, the dogs were euthanized by intravenous injection of 100 mg/kg of pentobarbital. The abdomen was incised again, and the transplanted regeneration scaffold (the tube and the fabrics) was surgically resected as a single block with the surrounding tissue of the aorta to provide a resected specimen for naked-eye or microscopic examination.

After naked-eye evaluation, the resected specimen was fixed in a 10% neutral formalin solution and was HE-stained or Elastica van Gieson (hereinafter, abbreviated to EG) stained by a standard approach to provide a microscopic thin slice specimen (4 μm). This thin slice specimen was observed under an optical microscope.

(3) Experimental results

The results of naked-eye observation revealed that the regenerated aorta performs a function as an aorta, i.e., the regenerated aorta has a thrombus-free lumen allowing the aortic blood to flow.

Figure 6A:
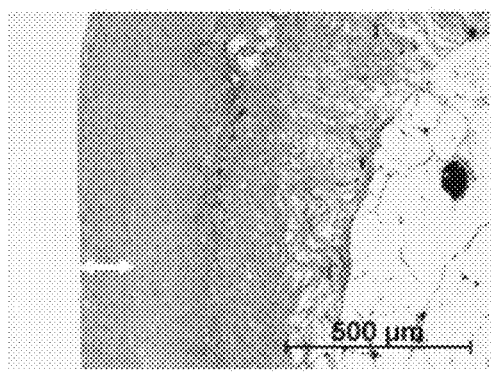
FIGS. 6A to 6G are photographs for drawings showing the results of investigation on whether a fabric constituting the medical base material according to the present invention can be used as a regeneration scaffold when the fabric is wrapped around the completely dissected aorta in dogs.
Figure 6E:
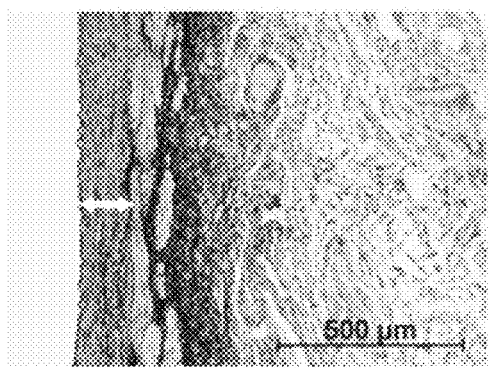
Figure 6B:
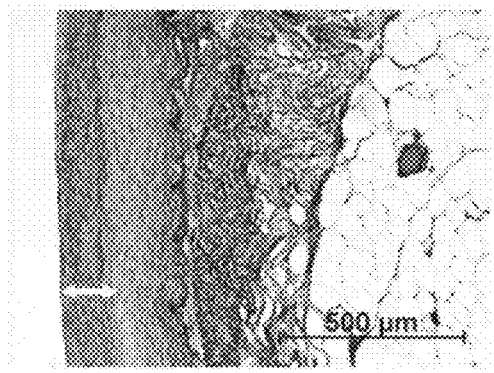
Figure 6F:
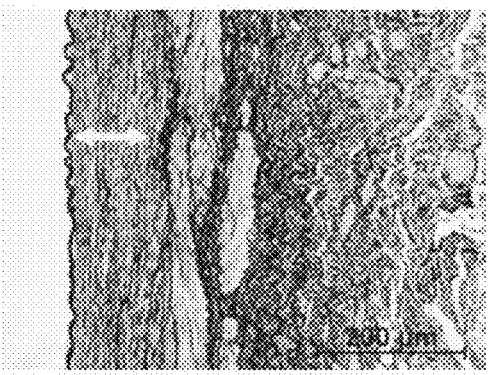
Figure 6C:
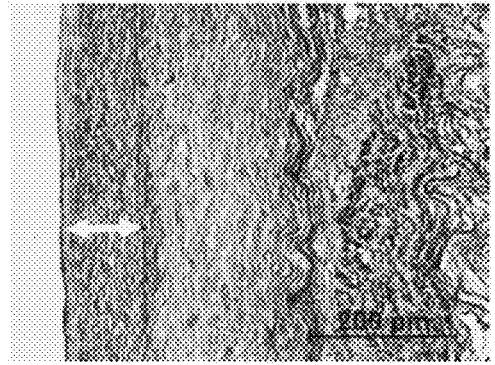
Figure 6G:
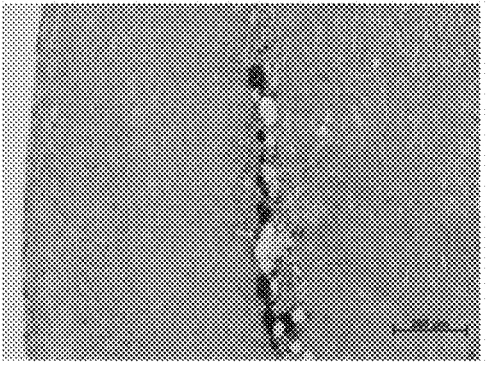
Figure 6D:
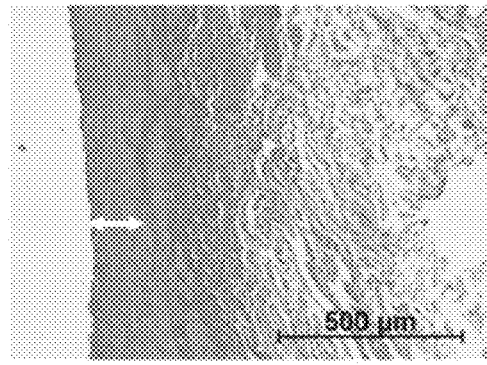

FIGS. 6A to 6G show the results of microscopic observation. FIGS. 6A to 6C are microscopic photographs of a regenerated aortic wall; FIG. 6A is that of HE staining; FIG. 6B is that of EG staining; and FIG. 6C is a partially enlarged view of FIG. 6B. FIGS. 6D to 6F are microscopic photographs of a natural aortic wall; FIG. 6D is that of HE staining; FIG. 6E is that of EG staining; and FIG. 6F is a partially enlarged view of FIG. 6E. The arrows in FIGS. 6C and 6F indicate the media layer of the aorta. FIG. 6G is an enlarged view (HE staining) of another portion of the same regenerated aortic wall.

As shown in FIG. 6A, the regenerated aorta was composed of an intima, a media, and an adventitia and was very similar to the structure of the natural aorta shown in FIG. 6D. As shown in FIGS. 6B and 6C, the regenerated media was rich in elastic fibers and smooth muscle cells as in the natural media. Furthermore, as shown in FIG. 6G, even if a small amount of the polymer remained, the artery wall was well regenerated.

These results demonstrated that an aorta having the ESD (LA/CL) fabric produced in Experiment 1 as an inner layer and the K (PLA) fabric as the outer layer was regenerated in a total tubular form. The results of Experiment 2 and Experiment 3 suggest that the K (PLA) fabric constituting the outer layer became a biological self-assembled reinforcement layer within a few weeks; the self-assembled reinforcement layer reinforced the ESD (LA/CL) fabric as the inner layer against the aortic blood pressure over a long period of time until its deterioration; and a media (which requires very long time for regeneration) having a sufficient strength against the aortic blood pressure was regenerated while the reinforcement layer reinforcing.

<Experiment 6> Perfomance comparison

The influence of the difference in materials constituting the outer layer of the medical base material on the performance was investigated by transplanting artificial blood vessels into arteries of dogs. Specifically, the experiment was carried out as follows.

(1) Experimental animal and its acclimation

Beagle dogs (adult, weight: 7 to 14 kg) purchased from Shimizu Experimental Animal Co., were used as the experimental animal. During the experimental period, the dogs were raised individually under standard conditions for at least one week before the experiment and were freely fed with standard dog feed and water.

(2) Production of artificial blood vessel

Artificial blood vessels having outer layers each made from a stereo complex polylactic acid and an artificial blood vessel having an outer layer made from a polylactic acid other than a stereo complex polylactic acid were produced for Samples 1 to 5 and for Comparative Sample, respectively, and the performance was compared. The produced artificial blood vessels were sterilized with ethylene oxide gas before use. The detail will now be described in detail.

1) Sample 1

Fabrics serving as an inner layer, an intermediate layer, and an outer layer were each rolled into a tubular shape, and the edges were sutured with 12 of a 6-0 polypropylene monofilament sutures to fit and unify the tubes into an artificial blood vessel sample (length: 30 mm, inner diameter: 7.5 mm) by hand.

Outer layer: Knitted fabric of a stereo complex polylactic acid fiber
Stereo complex polylactic acid molecular weight: about 200000
Crystalline melting point of stereo complex polylactic acid: 200° C. to 230° C.
Monofilament diameter: 18 to 22 μm (mainly 22 μm)
Number of monofilaments/twisted yarn: 60
Fiber interval of twisted yarns: 50 to 2000 μm
Number of turns of fabric: three times
Intermediate layer: Electrospun nonwoven fabric of PLA/CL (75%/25%) copolymer fiber
Fiber interval: 55 μm (use of a polymer spacer extending the fiber interval)
Fabric thickness: 180 μm
Number of turns of fabric: twice
Inner layer: Electrospun nonwoven fabric of 50% by weight of PLA/CL (75%/25%) fiber and 50% by weight of collagen fiber
Fiber diameter: 0.7 μm
Fiber interval: 11 μm
Fabric thickness: 480 μm 2) Sample 2
An artificial blood vessel sample (length: 35 mm, inner diameter: 5.5 mm) was produced as in Sample 1.
Outer layer: Knitted fabric of stereo complex polylactic acid fiber
Stereo complex polylactic acid molecular weight: about 200000
Crystalline melting point of stereo complex polylactic acid: 200° C. to 230° C.
Monofilament diameter: 16.5 μm
Number of monofilaments/twisted yarn: 48
Interval of twisted yarns: 240 μm
Number of turns of fabric: three times
Intermediate layer: Electrospun nonwoven fabric of PLA/CL (75%/25%)
Fiber interval: 55 μm (use of a spacer)
Fabric thickness: 180 μm
Number of turns of fabric: twice
Inner layer: Electrospun mixed nonwoven fabric of 50% by weight of PLA/CL (75%/25%) fiber and 50% by weight of collagen fiber
Fiber diameter: 0.7 μm
Fiber interval: 11 μm
Fabric thickness: 330 μm 3) Sample 3
An artificial blood vessel sample (length: 40 mm, inner diameter: 7.0 mm) was produced as in Sample 1.
Outer layer: Knitted fabric of stereo complex polylactic acid fiber
Stereo complex polylactic acid molecular weight: about 200000
Crystalline melting point of stereo complex polylactic acid: 200° C. to 230° C.
Monofilament diameter: 12.5 μm
Number of monofilaments/twisted yarn: 12
Fiber interval of twisted yarns: 1500 μm
Number of turns of fabric: three times
Intermediate layer: Electrospun nonwoven fabric of PLA/CL (75%/25%) copolymer fiber
Fiber interval: 55 μm (use of a spacer)
Fabric thickness: 180 μm
Number of turns of fabric: twice
Inner layer: Electrospun mixed nonwoven fabric of 50% by weight of PLA/CL (75%/25%) fiber and 50% by weight of collagen fiber
Fiber diameter: 0.8 μm
Fiber interval: 6.5 μm
Fabric thickness: 240 μm 4) Sample 4
An artificial blood vessel sample (length: 30 mm, inner diameter: 5.0 mm) was produced as in Sample 1.
Outer layer: Knitted fabric of stereo complex polylactic acid fiber
Stereo complex polylactic acid molecular weight: about 200000
Crystalline melting point of stereo complex polylactic acid: 200° C. to 230° C.
Monofilament diameter: 12.5 μm
Number of monofilaments/twisted yarn: 12
Interval of twisted yarns: 360 μm
Number of turns of fabric: three times
Intermediate layer: Electrospun nonwoven fabric of PLA/CL (75%/25%) copolymer fiber
Fiber interval: 42 μm (use of a polymer spacer extending the fiber interval)
Fabric thickness: 170 μm
Number of turns of fabric: three times
Inner layer: Electrospun nonwoven fabric of 50% by weight, of PLA/CL (75%/25%) fiber and 50% by weight of collagen fiber
Fiber diameter: 4.7 μm
Fiber interval: 35 μm (use of a spacer)
Fabric thickness: 120 μm 5) Sample 5
An artificial blood vessel sample (length: 30 mm, inner diameter: 5.0 mm) was produced as in Sample 1.
Outer layer: Knitted fabric of stereo complex polylactic acid fiber
Stereo complex polylactic acid molecular weight: about 150000
Crystalline melting point of stereo complex polylactic acid: 200° C. to 230° C.
Monofilament diameter: 16.5 μm
Number of monofilaments/twisted yarn: 36
Fiber interval of twisted yarns: 2.40 μm
Number of turns of fabric: once
Intermediate layer: Not included
Inner layer: Porous material produced by vacuum drying of a PLA/CL (50%/50%) solution
Pore diameter: 250 μm or less in 90% pores
Fabric thickness: 580 μm (including the outer layer)

6) Comparative Sample
An artificial blood vessel sample (length: 30 mm, inner diameter: 6.0 mm) was produced as in Sample 1.
Outer layer: Knitted fabric of L-polylactic acid fiber
L-polylactic acid fiber molecular weight: about 200000
Crystalline melting point of L-polylactic acid fiber: about 170° C. to 180° C.
Monofilament diameter: 16.5 μm
Number of monofilaments/twisted yarn: 12 Fiber interval of twisted yarns: 360 μm Number of turns of fabric: three times
Intermediate layer: Electrospun nonwoven fabric of PLA/CL (75%/25%) copolymer fiber
Fiber interval: 42 μm (use of a polymer spacer extending the fiber interval)
Fabric thickness: 170 μm
Number of turns of fabric: three times
Inner layer: Electrospun nonwoven fabric of PLA/CL (75%/25%) copolymer fiber
Fiber diameter: 4.7 μm
Fiber interval: 35 μm (use of a spacer)
Fabric thickness: 360 μm (3) Experimental method As in Experiment 4, the abdominal aorta (hereinafter, abbreviated as aorta) was peeled from the surrounding tissue, and the aorta was held with two forceps. The aorta was completed dissected between the forceps along the whole circumference of the aortic wall. The two stumps of the aorta were washed with heparin-physiological saline. An artificial blood vessel was placed between the two stumps of the aorta, and the edges of the aorta and the artificial blood vessel were anastomosed. That is, the artificial blood vessel stump and the aortic wall stump were sutured with 12 of a 6-0 polypropylene monofilament sutures. Finally, the peritoneal incision edges were sutured, then the abdominal incision wound was closed by two-layer suture. After the operation, anticoagulation was performed with 2000Units of low molecular heparin and 100 mg of aspirin or 1 mg of warfarin per day.

Ten months after the operation, the dog was euthanized by intravenous injection of 100 mg/kg of pentobarbital. The abdomen of the euthanized dog was incised again, and the transplanted artificial blood vessel was surgically resected as a single block with the surrounding tissue of the aorta to provide a resected specimen for microscopic examination.

The resected specimen was fixed in a 10% neutral formalin solution and was HE-stained or Elastica van Gieson (hereinafter, abbreviated to EG) stained by a standard approach to provide a microscopic thin slice specimen (4 µm). Thin slice specimen was observed under an optical microscope.

(4) Experimental results

The results of naked-eye observation for the sites in which the artificial blood vessels of Samples 1 to 5 and Comparative Sample were transplanted and harvested from the dogs and the results of microscopic observation for the resected specimens are briefly described below.

1) Results of Sample 1

Figure 7:
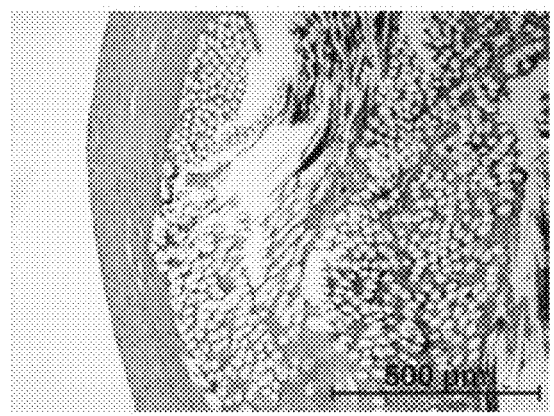
FIG. 7 is a photograph for a drawing showing the result when a medical base material (Sample 1) according to the present invention was transplanted in a dog.

In the naked-eye observation, abnormal findings, such as aneurysm and stenosis, were not recognized. The results of microscopic observation (HE staining) are shown in FIG. 7. As shown in FIG. 7, in the microscopic observation, many of the stereo complex polylactic acid fibers constituting the outer layer remained. In contrast, the PLA/CL fibers constituting the inner layer and the intermediate layer hardly remained.

Since the outer layer had a wide fiber interval and was made from a thick knitting yarn (twisted yarn consisting of 60 monofilaments), the luminal surface had relatively large irregularity. Accordingly, the risk of forming thrombi on the blood vessel wall should be high. However, the results were better than those of conventional artificial blood vessel bellows. The inner layer had adequate thickness and was relatively easy to sew. The overall evaluation was good.

2) Results of Sample 2

Figure 8:
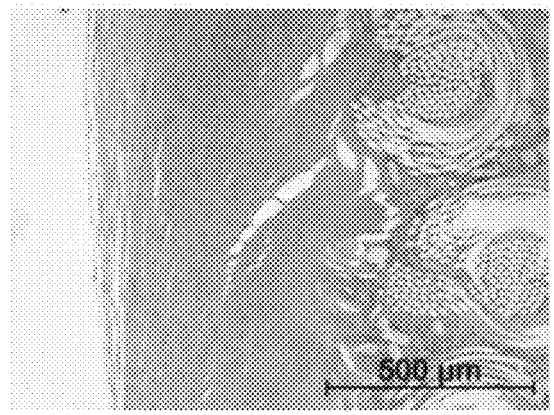
FIG. 8 is a photograph for a drawing showing the result when a medical base material (Sample 2) according to the present invention was transplanted in a dog.

In the naked-eye observation, abnormal, findings, such as aneurysm and stenosis, were not recognized. The results of microscopic observation (HE staining) are shown in FIG. 8. As shown in FIG. 8, in the microscopic observation, many of the stereo complex polylactic acid fibers constituting the outer layer remained. In contrast, the PLA/CL fibers constituting the inner layer and the intermediate layer hardly remained.

The outer layer formed spots depending on the state of overlapping thereof and was divided into a portion into which a nutrient blood vessel easily invades from the outside and a portion into which a nutrient blood vessel hardly invades. The inner layer was relatively easy to sew. The overall evaluation was good.

3) Results of Sample 3

Figure 9:
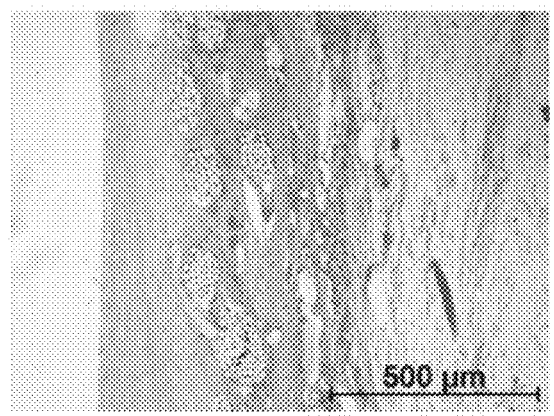
FIG. 9 is a photograph for a drawing showing the result when a medical base material (Sample 3) according to the present invention was transplanted in a dog.

In the naked-eye observation, abnormal findings, such as aneurysm and stenosis, were not recognized. The results of microscopic observation (HE staining) are shown in FIG. 9. As shown in FIG. 9, in the microscopic observation, many of the stereo complex polylactic acid fibers constituting the outer layer remained. In contrast, the PLA/CL fibers constituting the inner layer and the intermediate layer hardly remained.

Since the fabric constituting the outer layer had a sufficiently wide fiber interval, the invasion of a nutrient blood vessel from the outside was good. Although spots depending on the state of partial overlapping of the layers were observed, the degree thereof was negligible. The overall evaluation was good.

4) Results of Sample 4

In the naked-eye observation, abnormal findings, such as aneurysm and stenosis, were not recognized. In the microscopic observation (not shown), many of the stereo complex polylactic acid fibers constituting the outer layer remained. In contrast, the PLA/CL fibers constituting the inner layer and the intermediate layer hardly remained.

Since the fabric constituting the outer layer had a sufficiently wide fiber interval, the invasion of a nutrient blood vessel from the outside was good. Although spots depending on the state of partial overlapping of the layers were observed, the degree thereof was negligible. In the inner layer, the fiber interval and fiber thickness were adequate. In addition, the inner layer had a thickness within an appropriate range. The overall evaluation was good.

5) Results of Sample 5

Figure 10:
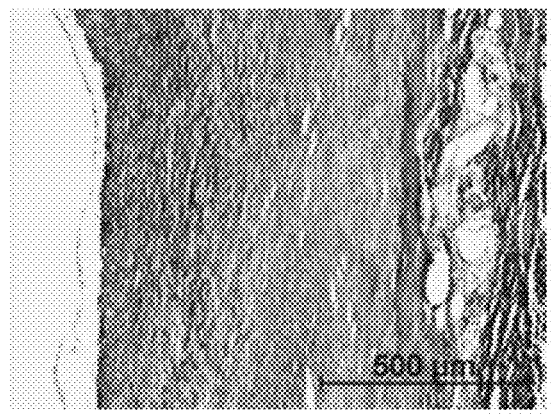
FIG. 10 is a photograph for a drawing showing the result when a medical base material (Sample 5) according to the present invention was transplanted in a dog.

In the naked-eye observation, abnormal findings, such as aneurysm and stenosis, were not recognized. The results of microscopic observation (EG staining) are shown in FIG. 10. As shown in FIG. 10, it was demonstrated that elastic fibers and smooth muscle cells were regenerated and that the artery wall was well regenerated. The artery by surgical suture resembled a natural one. The invasion of a nutrient blood vessel from the outside was also good probably because the fabric constituting the outer layer had a sufficiently wide fiber interval. The results of comprehensive evaluation were the best among Samples.

6) Results of Comparative Sample

Figure 11A:
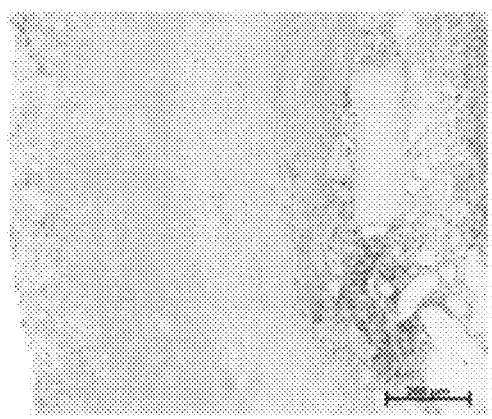
FIGS. 11A and 11B are photographs for drawings showing the results when an existing medical base material (Comparative Sample) was transplanted in a dog.
Figure 11B:
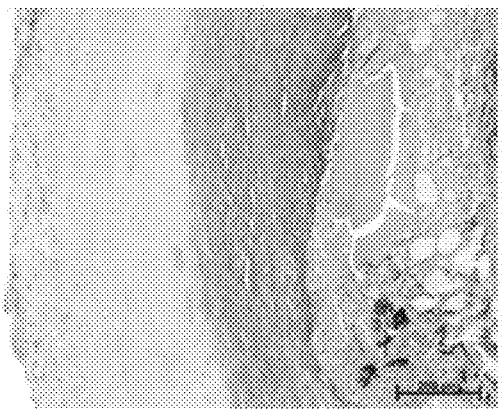

In the naked-eye observation, formation of aneurysm was recognized overall, and thrombi were observed on the blood vessel wall. FIGS. 11A and 11B show the results of microscopic observation. FIG. 11A shows the results of HE staining, and FIG. 11B shows the results of EG staining. As shown in FIGS. 11A and 11B, in the microscopic observation, new and old thrombi, scarring, and partial inflammation were recognized on the blood vessel wall. Accordingly, the overall evaluation was poor probably because of early deterioration in the strength of the outer layer.

In addition to Samples 1 to 5 and Comparative Sample, other samples having a variety of compositions were produced by combining the fabrics for the outer layer shown in Table 1, the fabrics for the intermediate layer shown in Table 2, and the highly biocompatible fabrics for the inner layer shown in Table 3. The samples were transplanted in dogs, and changes with time were observed with an ultrasonic diagnostic apparatus over at least six months (18 months at the longest). The results of observation are collectively shown in Table 4. The column of Sample in Table 1 shows the composition, the monofilament diameter, the number of monofilaments for twisted yarn, the production process, the interval of twisted yarns, the thickness, and the number of turns of each outer layer in success Samples.

TABLE 1

| Outer layer | Sample | Comparative Sample |
|---|---|---|
| Composition of fabric | Stereo complex polylactic acid 26 fabrics in three groups: (a) Knitted fabric: 20 (b) Woven fabric: 1 (c) Nonwoven fabric: 5 | Material other than stereo complex polylactic acid 24 fabrics in four groups: (a) PLLA: 9 (b) PDLA: 5 (c) Mere mixture of PLLA and PDLA: 5 (d) Mere copolymer of PLLA and PDLA: 5 |
| Monofilament diameter | 10 to 25 μm (0.3 to 5 μm in 70% or more in electrospinning) | Same as on the left |
| Number of monofilaments/twisted yarn | 12 to 60 (knitting and weaving) | Same as on the left |
| Production process | Knitting, weaving, electrospinning, or combination thereof with needle punching | Same as on the left |
| Interval of twisted yarns (In some of electrospun nonwoven fabrics, a polymer for extending the fiber interval was used) | Woven fabric or knitted fabric: 50 to 2000 μm Nonwoven fabric: 800 μm (needle punch pore size) | Same as on the left |
| Thickness | Woven fabric or knitted fabric: 60 to 600 μm Nonwoven fabric: 25 to 47 μm | Same as on the left |
| Number of turns | One to four times | Same as on the left |

TABLE 2

| Intermediate layer | |
|---|---|
| Composition of fabric | (a) PLA/CL (75/25) (b) PLLA (c) PLA/CL (50/50) |
| Fiber diameter (median) | 0.4 to 15 (μm) |
| Production process | (a) Electrospinning (b) Melt-blow |
| Fiber interval (In some of fabrics, a polymer for extending the fiber interval was used) | 32 to 70 (μm) |
| Thickness | 30 to 200 (μm) |
| Number of turns | Zero to four (times) (Basically, the intermediate layer is overlaid on an outer layer and is wrapped on an inner layer.) |

TABLE 3

| Inner layer | |
|---|---|
| Composition of fabric | (a) 70% PLA/CL (75/25) + 30% collagen (b) 50% PLA/CL (75/25) + 50% collagen (c) PLA/CL (75/25) alone (d) PLLA (e) PLA/CL (50/50) |
| Fiber diameter (median) | 0.1 to 7 (μm) |
| Production process | (a) Electrospinning (b) Melt-blow (c) Vacuum drying of copolymer solution |
| Fiber interval (In some of fabrics, a polymer for extending the fiber interval was used) | 6.0 to 55 μm |
| Thickness | 100 to 560 (μm) |
| Inner diameter | 4.0 to 7.0 (mm) |

TABLE 4

| | Material of outer layer | |
|---|---|---|
| | Stereo complex polylactic acid | Material other than stereo complex polylactic acid |
| No abnormality within observation period | 26/26 | 0/24 |

As shown in Table 4, in artificial blood vessels (26 in total) using a stereo complex polylactic acid in the outer layer, artery regeneration with abnormal course, such as arteriosclerosis, stenosis/occlusion, rupture, and aneurysm, was not recognized at all in the observation period of 6 to 16 months. In contrast, in all the artificial blood vessels (24 in total) using a polylactic acid other than a stereo complex polylactic acid, abnormalities were observed in the observation period (in particular, in 22 specimens, abnormalities were observed within 6 months).

Thus, an aorta was completely regenerated by transplanting an artificial blood vessel including an outer layer made from a stereo complex polylactic acid. In contrast, an artificial blood vessel including an outer layer made from another polylactic acid similarly starting from lactic acid hardly regenerated an aorta. That is, it was demonstrated that the difference in the polylactic acid constituting the outer layer relates to the aorta regeneration.

The medical base material of the present invention is not limited to the embodiments described above. For example, in addition to the tubular shapes shown FIGS. 1A and 1B, and FIGS. 2A and 2B, for example, a sheet-shaped medical base material can be also used. A sheet-shaped medical base material is, for example, wrapped around an affected area to regenerate it. In this medical base material, the inner layer (innermost layer) to be arranged at the closest position to the affected area enhances regeneration of the affected area by engraftment of cells such as endothelial cells. In contrast, the layer on the outer side of the innermost layer, i.e., the layer to be arranged on the adventitial side of a cardiovascular system, maintains the strength of the medical base material until the regeneration of the affected area and is formed in a porous form such that a nutrient blood vessel reaches the innermost layer or enters the vicinity of the innermost layer. Accordingly, the layer assists the growth of a nutrient blood vessel and raising of the engrafted cells such as endothelial cells and enhances regeneration of the affected area.

The medical base material of the present invention may include a layer, in addition to the outer layer, the inner layer, and the intermediate layer shown in FIGS. 1A and 1B, and FIGS. 2A and 2B, as needed. For example, in the case of anastomosing the medical base material to an aorta, a protective layer for protecting the anastomosis site may be provided. Alternatively, multiple outer layers may be disposed around the inner layer.

Furthermore, the outer layer, the inner layer, and the intermediate layer may be each a thin porous material other than a fabric. In the case of a porous material, the layers can be produced by any known method.

In the embodiments described above, although the fabric was sewed into a tubular shape, a tubular fabric may be produced by, for example, a method such as electrospinning or with a flat-knitting machine in advance.

INDUSTRIAL APPLICABILITY

The medical base material of the present invention is suitable for regeneration of the cardiovascular system receiving the pressure of blood and is particularly suitable above all for regeneration of a thick artery receiving high pressure.

REFERENCE SIGNS LIST 1, 2 medical base material
11, 21 outer layer.
12, 22 inner layer
23 intermediate layer

The invention claimed is:

1. A blood vessel regeneration device having a sheet shape or a tube shape and being used for regeneration of an entire layer of a blood vessel of a cardiovascular system by being sutured onto an edge of a defected blood vessel or configured to be wrapped around an affected blood vessel wall in a body, wherein
the blood vessel regeneration device has a multilayer structure comprising:
an inner layer positioned on an intimal side of the cardiovascular system and made from a bioabsorbable polymer; and
an outer layer positioned on an adventitial side of the cardiovascular system from the inner layer and made from a material comprising at least 50% by weight of a stereo complex polylactic acid, wherein
the inner layer has higher bioabsorability than the outer layer; and
the outer layer positioned on the adventitial side of the cardiovascular system from the inner layer is formed in a porous form such that a nutrient blood vessel reaches the inner layer or enters a vicinity of the inner layer.

2. The blood vessel regeneration device according to claim 1, wherein the outer layer comprises a fabric made from a fiber material comprising at least 50% by weight of the stereo complex polylactic acid.

3. The blood vessel regeneration device according to claim 2, wherein the fabric is a woven fabric or a knitted fabric.

4. The blood vessel regeneration device according to claim 2, wherein the fabric is made from a fiber material having a fiber diameter median of 0.1 to 40 μm.

5. The blood vessel regeneration device according to claim 2, wherein the fabric is a nonwoven fabric having a median distance from a stump of a first fiber to a stump of a second fiber adjacent to the first fiber of 5 to 1000 μm.

6. The blood vessel regeneration device according to claim 2, wherein the fabric is a woven or knitted fabric having a median distance from a stump of a first fiber to a stump of a second fiber adjacent to the first fiber of 15 to 2000 μm.

7. The blood vessel regeneration device according to claim 1, wherein the inner layer comprises at least one material selected from the group consisting of polyglycolic acid, a copolymer of lactic acid and caprolactone, L-polylactic acid, D-polylactic acid, a copolymer of glycolic acid and lactic acid, gelatin, collagen, and elastin.

8. The blood vessel regeneration device according to claim 7, wherein the inner layer comprises a highly biocompatible fabric made from a fiber material.

9. The blood vessel regeneration device according to claim 1, wherein the multilayer structure further comprises an intermediate layer between the outer layer and the inner layer, wherein the intermediate layer is overlaid on the outer layer and wrapped on the inner layer.

10. The blood vessel regeneration device according to claim 9, wherein the outer layer comprises a fiber having a fiber interval of 1 to 4 mm.

11. The blood vessel regeneration device according to claim 1, wherein the multilayer structure comprises at least two outer layers disposed around the inner layer.

12. The blood vessel regeneration device according to claim 11, wherein the outer layers comprise a fiber having a fiber interval of 1 to 4 mm.

* * * * *